(12) United States Patent
Rivard et al.

(10) Patent No.: US 8,271,096 B2
(45) Date of Patent: Sep. 18, 2012

(54) PRE-SELECTED COMPRESSION LEAD ANCHORING DEVICE

(75) Inventors: Adam J. Rivard, Blaine, MN (US); Kevin E. Verzal, Minneapolis, MN (US); David A. Durand, Osceola, WI (US); David R. Wulfman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 267 days.

(21) Appl. No.: 12/265,290

(22) Filed: Nov. 5, 2008

(65) Prior Publication Data

US 2009/0125061 A1   May 14, 2009

Related U.S. Application Data

(60) Provisional application No. 60/986,922, filed on Nov. 9, 2007, provisional application No. 60/986,915, filed on Nov. 9, 2007, provisional application No. 60/986,911, filed on Nov. 9, 2007.

(51) Int. Cl.
*A61N 1/05* (2006.01)
(52) U.S. Cl. .......... 607/116; 607/126; 606/232
(58) Field of Classification Search .......... 607/116, 607/126; 606/232; 29/557
See application file for complete search history.

(56) References Cited

U.S. PATENT DOCUMENTS

| | | | |
|---|---|---|---|
| 4,266,552 A | 5/1981 | Dutcher et al. | |
| 4,276,882 A | 7/1981 | Dickhudt et al. | |
| 4,287,891 A | 9/1981 | Peters | |
| 4,387,727 A | 6/1983 | Sandstrom | |
| 4,437,475 A | 3/1984 | White | |
| 4,516,584 A | 5/1985 | Garcia | |
| 4,538,623 A | 9/1985 | Proctor et al. | |
| 4,553,961 A * | 11/1985 | Pohndorf et al. | 604/175 |
| 4,613,329 A | 9/1986 | Bodicky | |
| 4,615,472 A | 10/1986 | Nash | |
| 4,672,979 A | 6/1987 | Pohndorf | |
| 4,676,782 A | 6/1987 | Yamamoto et al. | |
| 4,683,895 A | 8/1987 | Pohndorf | |
| 4,768,523 A | 9/1988 | Cahalan et al. | |
| 4,906,233 A | 3/1990 | Moriuchi et al. | |
| 5,036,862 A | 8/1991 | Pohndorf | |
| 5,107,856 A | 4/1992 | Kristiansen et al. | |
| 5,129,405 A | 7/1992 | Milijasevic et al. | |
| 5,152,298 A | 10/1992 | Kreyenhagen et al. | |

(Continued)

OTHER PUBLICATIONS

"Suture Sleeve with Removable Fins", Technical Disclosure from www.ip.com, No. IPCOM000125732D, published Jun. 15, 2005, full document available at http://www.ip.com/pubview/IPCOM000125732D, 4 pages.

(Continued)

*Primary Examiner* — Niketa Patel
*Assistant Examiner* — Alyssa M Alter
(74) *Attorney, Agent, or Firm* — Faegre Baker Daniels LLP

(57) ABSTRACT

An implantable medical system for anchoring a medical lead implanted in a patient includes a medical lead, an anchoring device received coaxially over the medical lead, and at least one fastener secured circumferentially about the anchoring device to cause compression of the anchoring device on the medical lead. The anchoring device includes an elastomeric sleeve having a substantially elongate, hollow, and tubular body and a compression governor coaxially secured about the elastomeric sleeve. The compression governor is adapted to limit compressive forces exerted on the lead by the anchoring device at a predetermined limit and provides a visual indicator that the predetermined limit has been reached.

17 Claims, 11 Drawing Sheets

U.S. PATENT DOCUMENTS

| | | | |
|---|---|---|---|
| 5,242,431 A | 9/1993 | Kristiansen | |
| 5,257,975 A | 11/1993 | Foshee | |
| 5,273,053 A | 12/1993 | Pohndorf | |
| 5,376,108 A | 12/1994 | Collins et al. | |
| 5,423,763 A | 6/1995 | Helland et al. | |
| 5,476,493 A | 12/1995 | Muff | |
| 5,549,619 A | 8/1996 | Peters et al. | |
| 5,584,874 A * | 12/1996 | Rugland et al. | 607/132 |
| 5,603,730 A | 2/1997 | Romkee | |
| 5,628,780 A | 5/1997 | Helland et al. | |
| 5,674,273 A | 10/1997 | Helland | |
| 5,683,403 A | 11/1997 | Adams et al. | |
| 5,683,446 A | 11/1997 | Gates | |
| 5,709,644 A | 1/1998 | Bush | |
| 5,735,891 A | 4/1998 | White | |
| 5,746,722 A | 5/1998 | Pohndorf et al. | |
| 5,824,032 A | 10/1998 | Belden | |
| 5,827,296 A | 10/1998 | Morris et al. | |
| 5,843,146 A | 12/1998 | Cross, Jr. | |
| 5,876,429 A | 3/1999 | Schroeppel | |
| 5,957,968 A * | 9/1999 | Belden et al. | 607/126 |
| 6,002,969 A | 12/1999 | Machek et al. | |
| 6,259,953 B1 | 7/2001 | Lucchesi et al. | |
| 6,473,654 B1 | 10/2002 | Chinn | |
| 6,554,802 B1 | 4/2003 | Pearson et al. | |
| 6,592,553 B2 | 7/2003 | Zhang et al. | |
| 6,901,287 B2 | 5/2005 | Davis et al. | |
| 6,921,295 B2 | 7/2005 | Sommer | |
| 6,985,777 B2 | 1/2006 | Tsuboi et al. | |
| 7,082,337 B2 | 7/2006 | Sommer et al. | |
| 7,184,841 B1 | 2/2007 | Bodner et al. | |
| 7,218,972 B2 | 5/2007 | Rodriguez | |
| 7,242,986 B2 | 7/2007 | Rodriguez | |
| 7,248,930 B1 | 7/2007 | Woloszko et al. | |
| 7,398,125 B2 | 7/2008 | Osypka et al. | |
| 2003/0050668 A1 | 3/2003 | Lee | |
| 2003/0195600 A1 | 10/2003 | Tronnes et al. | |
| 2003/0220678 A1 | 11/2003 | Tronnes et al. | |
| 2004/0059403 A1 | 3/2004 | Massullo | |
| 2004/0199234 A1 * | 10/2004 | Rodriguez | 607/116 |
| 2004/0254623 A1 | 12/2004 | Rodriguez et al. | |
| 2005/0080470 A1 | 4/2005 | Westlund et al. | |
| 2005/0177220 A1 | 8/2005 | Iaizzo et al. | |
| 2006/0235484 A1 | 10/2006 | Jaax et al. | |
| 2006/0264803 A1 | 11/2006 | Lui et al. | |
| 2007/0078399 A1 | 4/2007 | Olson | |
| 2009/0125058 A1 | 5/2009 | Bodner et al. | |
| 2009/0125059 A1 | 5/2009 | Verzal et al. | |
| 2009/0125060 A1 | 5/2009 | Rivard et al. | |

OTHER PUBLICATIONS

"Pacing Lead Stabilizer with Modified Slit Geometry", Technical Disclosure from www.ip.com, No. IPCOM000130753D, published Nov. 3, 2005, full document available at http://www.ip.com/pubview/IPCOM000125732D, 6 pages.

* cited by examiner

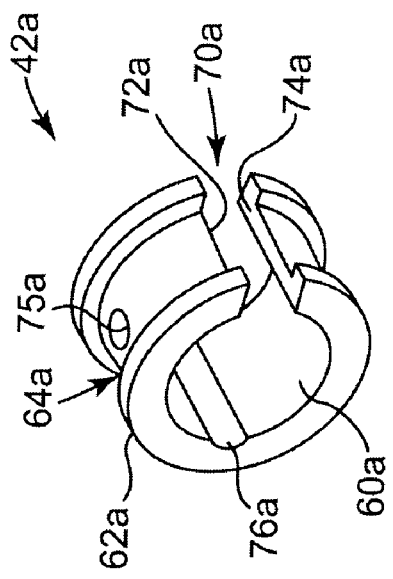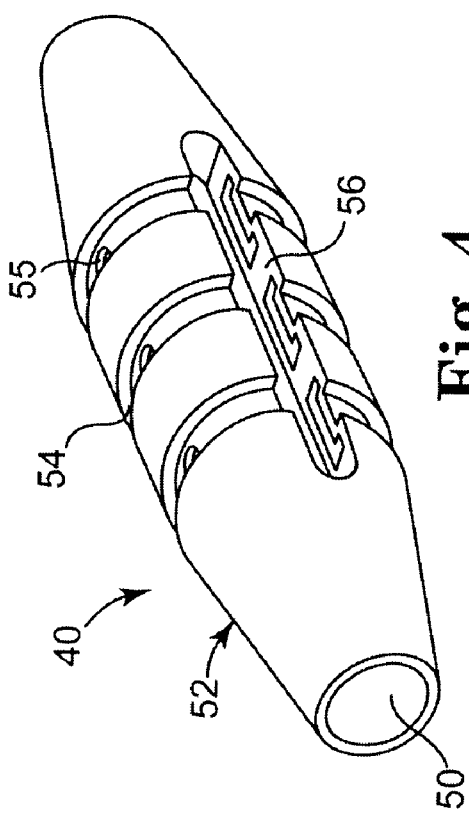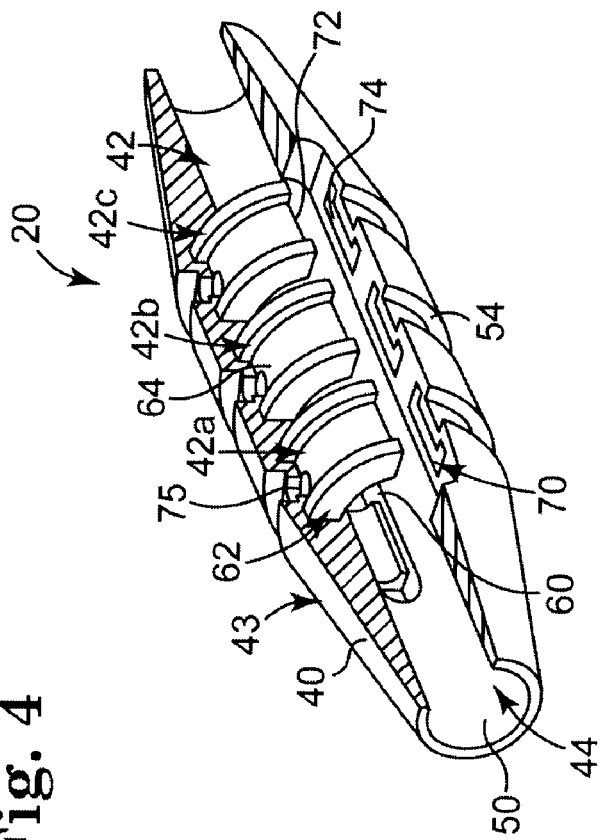

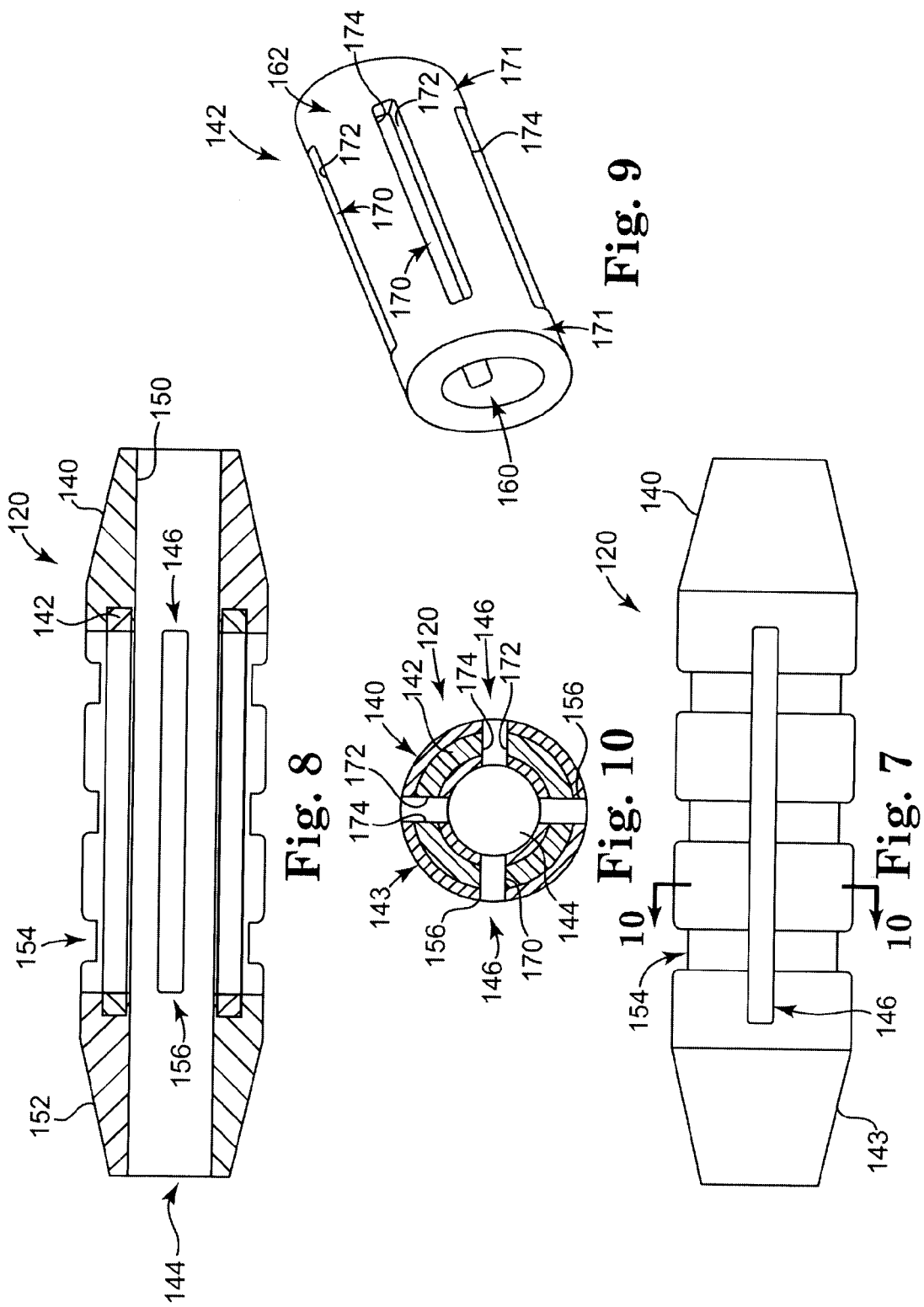

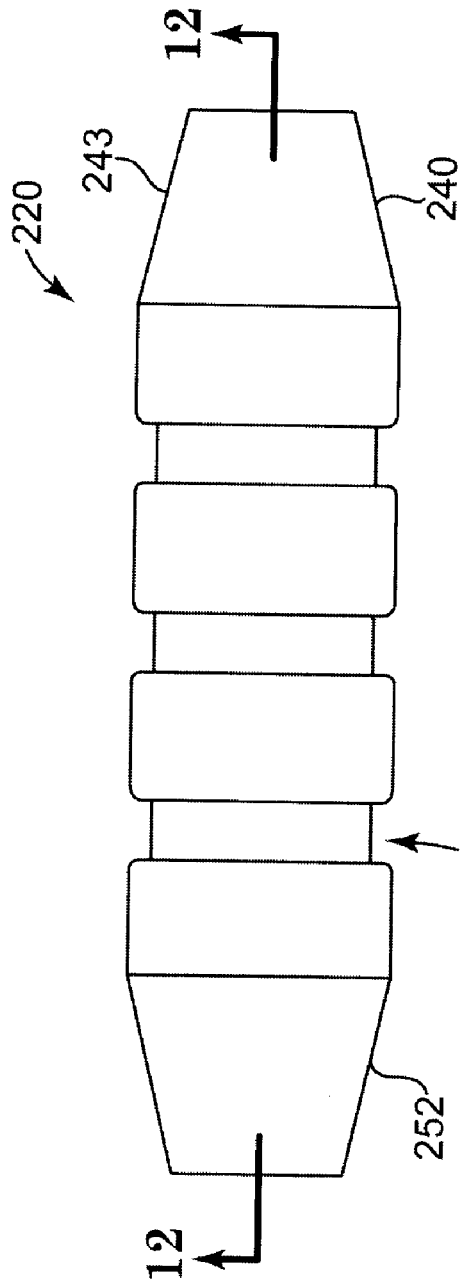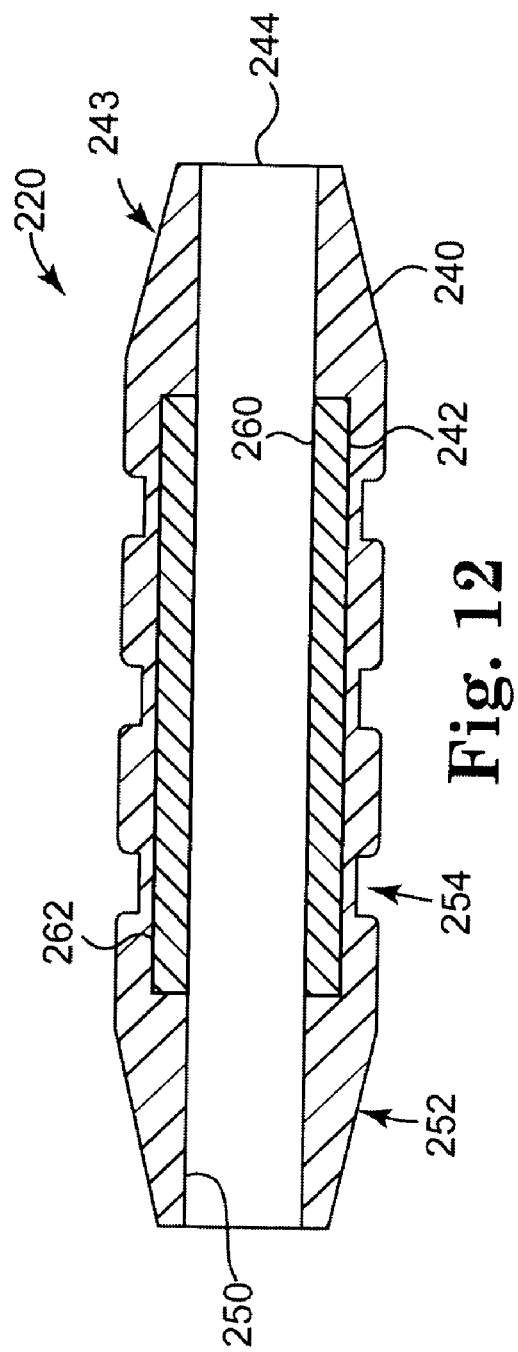
Fig. 11
Fig. 12

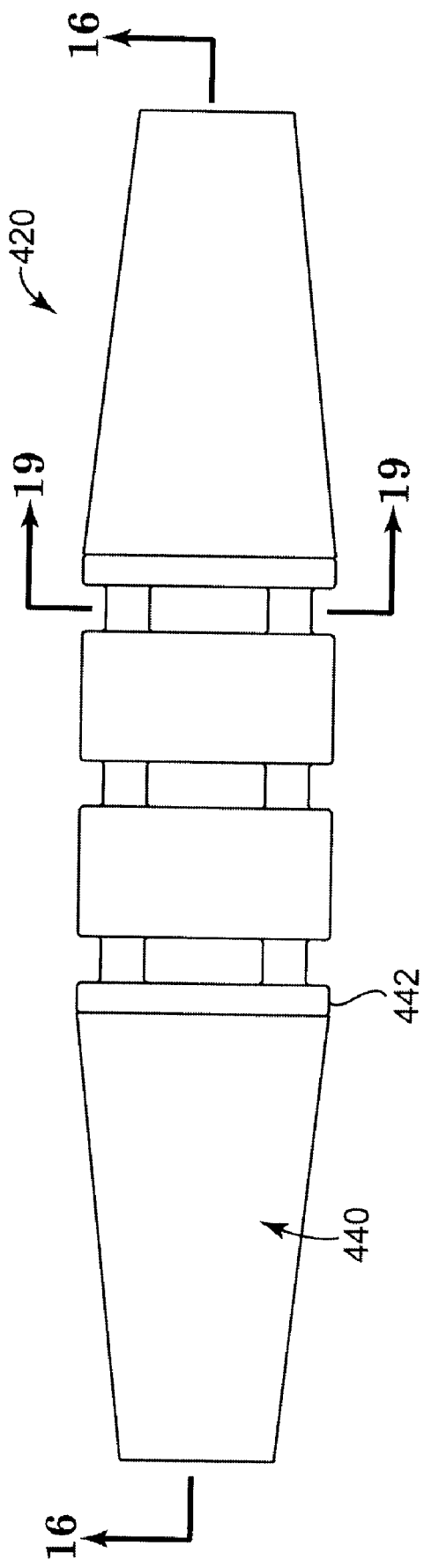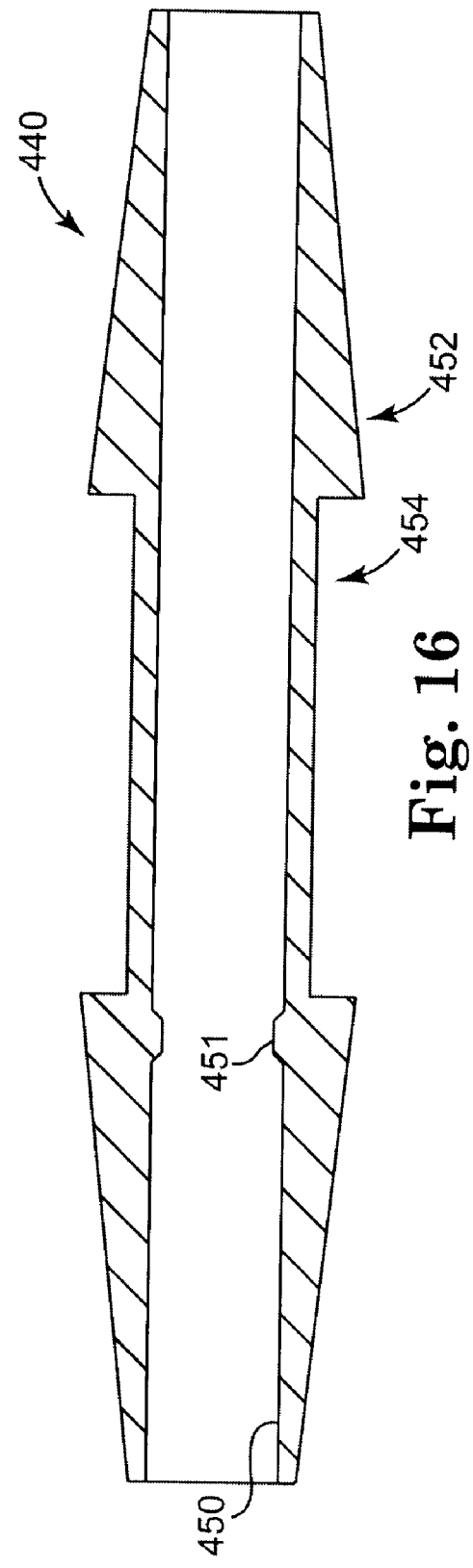
Fig. 15
Fig. 16

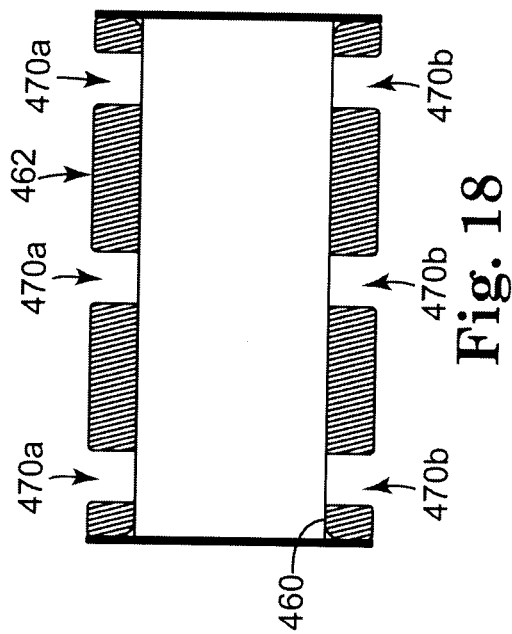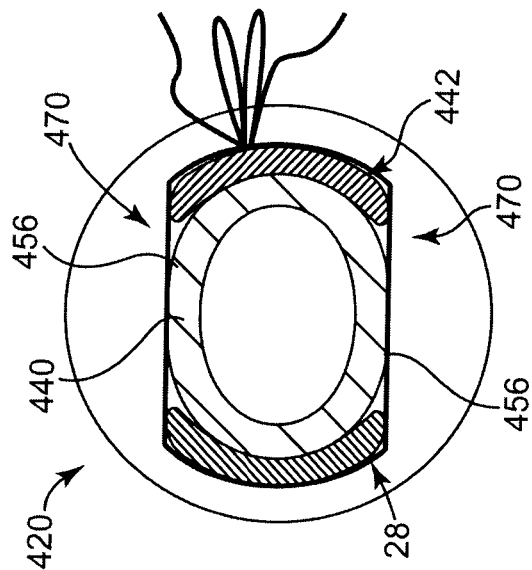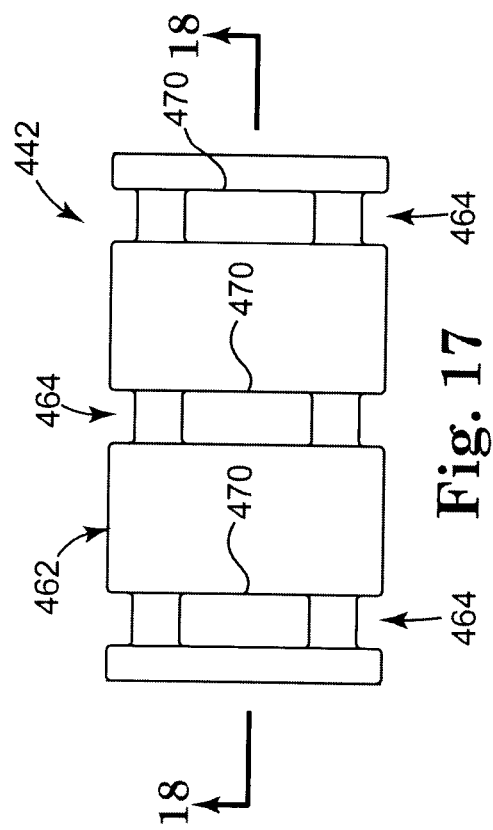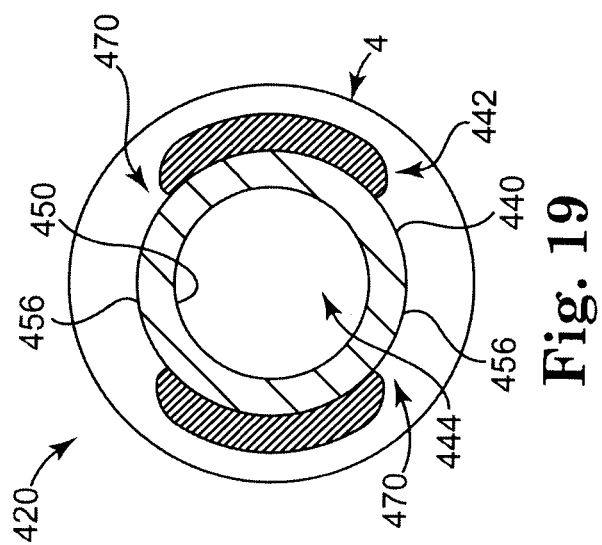

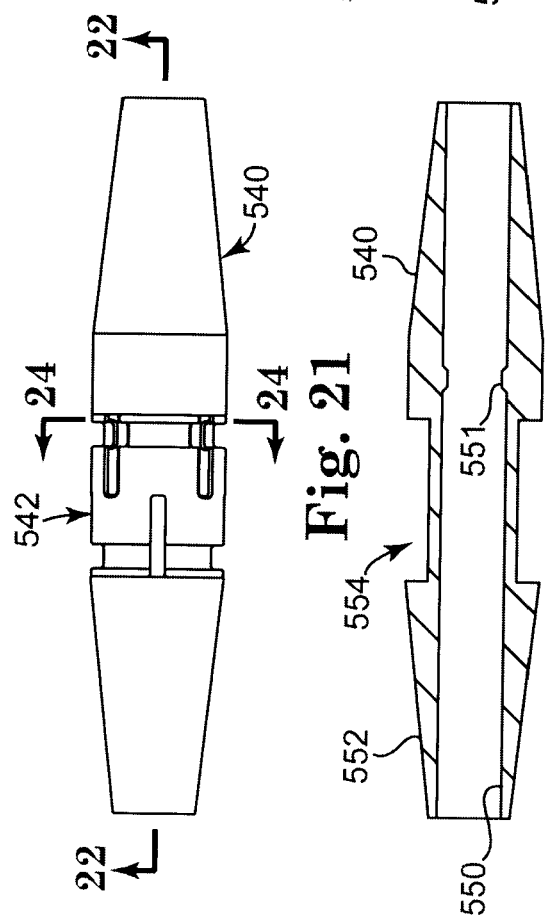
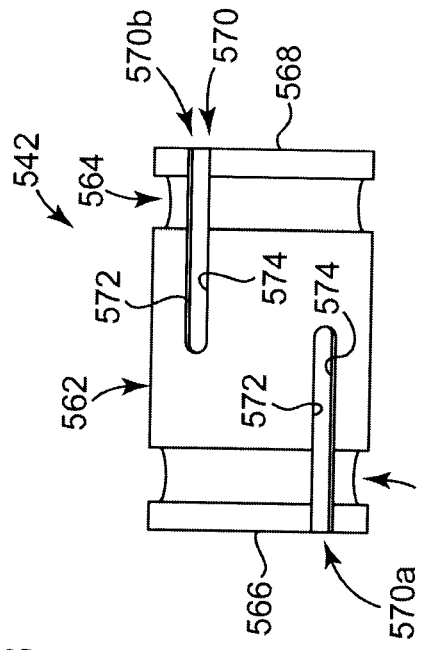
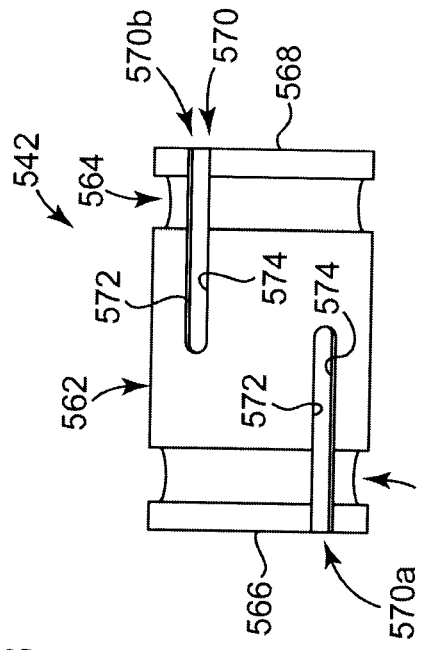
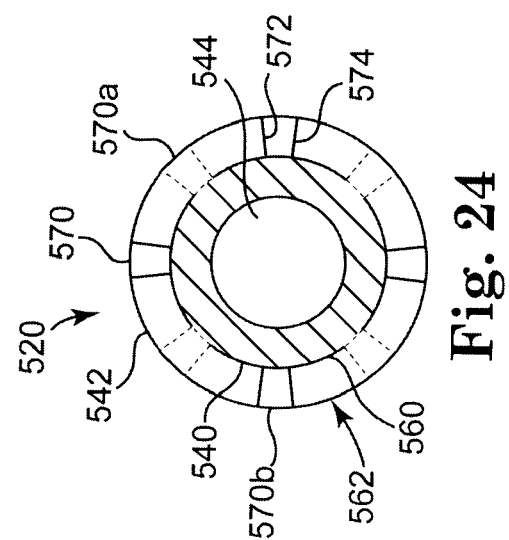
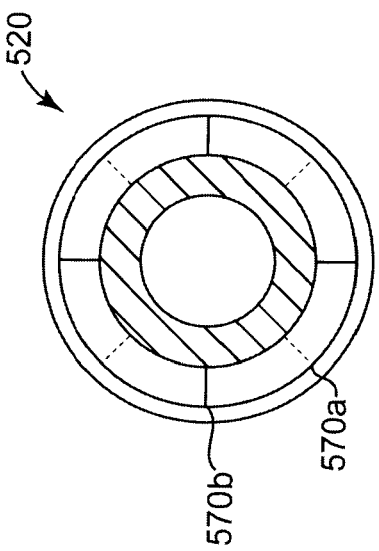

PRE-SELECTED COMPRESSION LEAD ANCHORING DEVICE

CROSS-REFERENCE TO RELATED APPLICATIONS

This application claims priority under 35 U.S.C. §119(e) to U.S. Provisional Patent Application No. 60/986,922, filed on Nov. 9, 2007, entitled "PRE-SELECTED COMPRESSION LEAD ANCHORING DEVICE," U.S. Provisional Patent Application No. 60/986,915, filed on Nov. 9, 2007, entitled "COMPRESSION MEMBER SUTURE SLEEVE," and U.S. Provisional Patent Application No. 60/986,911, filed on Nov. 9, 2007, entitled "COMPRESSION CONTROL LEAD ANCHORING DEVICE," all of which are incorporated herein by reference in their entirety.

TECHNICAL FIELD

The present invention relates generally to suture sleeves for anchoring medical leads to tissue of a patient. More specifically, the present invention relates to suture sleeves having compression control features.

BACKGROUND

Medical leads are secured to a patient's tissue in a variety of applications using anchoring devices, including those commonly referred to as suture sleeves. For example, in many applications, an electrical lead connected to a cardiac rhythm management (CRM) device, such as a pacemaker, is secured to patient tissue at a vein entry site or other location to help prevent both acute and chronic lead migration and dislodgement. In particular, the leads are anchored in place by securing a suture sleeve about the insulation of the lead and suturing the suture sleeve to the patient's tissue.

SUMMARY

Some aspects relate to an implantable medical system for anchoring a medical lead implanted in a patient. The system includes a medical lead, an anchoring device received coaxially over the medical lead, and at least one fastener secured circumferentially about the anchoring device to cause compression of the anchoring device on the medical lead. The anchoring device includes an elastomeric sleeve having a substantially elongate, hollow, and tubular body and a compression governor coaxially secured about the elastomeric sleeve. The compression governor is adapted to limit compressive forces exerted on the lead by the anchoring device at a predetermined limit and provides a visual indicator that the predetermined limit has been reached.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 shows a sleeve of the anchoring device of FIG. 2 from an isometric view.

FIG. 5. shows a portion of a compression governor of the anchoring device of FIG. 2 from an isometric view.

FIG. 6 shows the anchoring device of FIG. 2 with a quarter portion of the sleeve removed.

FIG. 7 is a front view of another anchoring device of the system of FIG. 1, according to some embodiments of the invention.

FIG. 8 is a cross-sectional view of the anchoring device of FIG. 7.

FIG. 9 shows a compression governor of the anchoring device of FIG. 7 from an isometric view.

FIG. 10 shows the anchoring device of FIG. 7 in transverse cross-section taken along line 10-10 of FIG. 7.

FIG. 11 is a front view of another anchoring device of the system of FIG. 1, according to some embodiments of the invention.

FIG. 12 is a cross-sectional view of the anchoring device of FIG. 11.

FIG. 15 is a top view of another anchoring device suitable for use with the anchoring system of FIG. 1, according to some embodiments of the invention.

FIG. 16 shows a cross-section of a sleeve of the anchoring device of FIG. 14 taken along line 16-16 of FIG. 15.

FIG. 17 is a top view of a compression governor of the anchoring device of FIG. 15.

FIG. 18 shows a cross-section of the compression governor of FIG. 16 taken along line 18-18 of FIG. 17.

FIGS. 19 and 20 show transverse cross-sections of the anchoring device of FIG. 15 taken along line 19-19 of FIG. 15.

FIG. 21 is a top view of another anchoring device suitable for use with the anchoring system of FIG. 1, according to some embodiments of the invention.

FIG. 22 shows only a sleeve of the anchoring device of FIG. 21 in a cross-section taken along line 22-22 of FIG. 21.

FIG. 23 is a top view of a compression governor of the anchoring device of FIG. 21.

FIGS. 24 and 25 are cross-sectional views taken along line 24-24 of FIG. 21.

Figure 1:
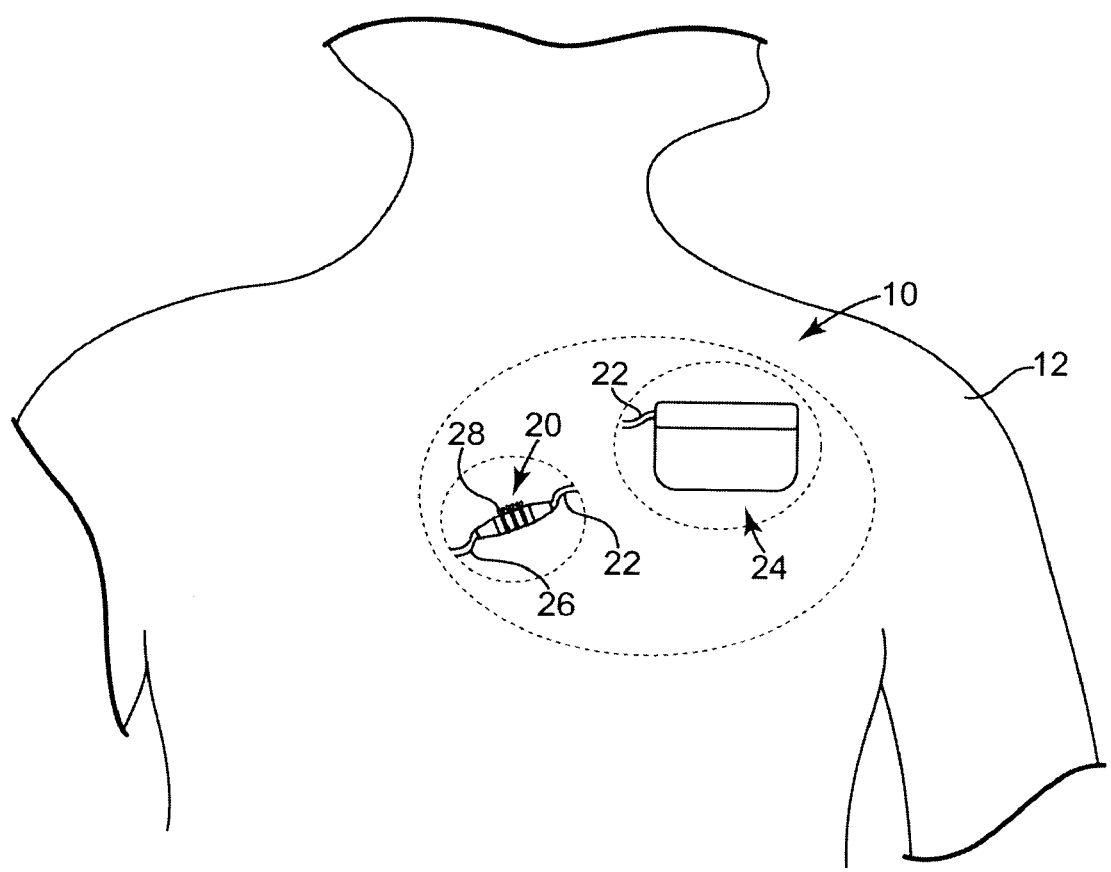
FIG. 1 is a schematic view of an anchoring system implanted in a patient's body, according to some embodiments of the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a simplified view of an implanted medical system 10 implanted in a patient's body 12 in accordance with various embodiments of the invention. The system 10 includes an anchoring device or suture sleeve 20, a medical device lead 22, and an implanted medical device (IMD) 24 connected to the lead 22. In some embodiments, the IMD 24 is a cardiac rhythm management (CRM) device (e.g., a pacemaker and/or defibrillator) or other therapeutic device (e.g., a drug pump), implanted in the body 12.

In some embodiments, the lead 22 is an electrical lead of a type suitable for use with CRM devices. The lead 22 includes one or more inner conductors (not shown) or other internal features and an outer, insulating sheath 26 extending over the internal features of the lead 22. In some embodiments, the lead 22 includes electrodes (not shown) or other features for stimulating or sensing functionality. The lead 22 is characterized by a maximum radial crushing force or a maximum compressive force that the lead 22 can withstand prior to sustaining damage.

In some applications, the anchoring device 20 is positioned over the insulating sheath 26 or other portion of the lead 22 and serves to stabilize the lead 22 at or near a vein entry site (not shown) to help prevent both acute and chronic lead migration and dislodgement. The anchoring device 20 is compressed onto the lead 22, for example by securing fasteners such as sutures 28 about the anchoring device 20. The sutures 28 are often times manually secured about the anchoring device 20 by a physician using some tension or tying force on the sutures 28. The tying force can vary from about 1 to about 8 pounds or more. Although sutures and manual methods of tying sutures are referenced herein, other fastening means and methods, spring clips or automatic suture tying devices, for example, are also contemplated and the description should be read accordingly.

As described in greater detail below, various embodiments of the anchoring device 20 are adapted to help minimize deformation or other damage to the insulating sheath 26 and internal features (e.g., the conductors) of the lead 22. In particular, the lead 22 can be damaged by the sutures 28. For example, the conductors and/or insulative sheath 26 can be damaged if there are sufficiently high and/or concentrated radial forces at the interface between the lead 22 and the anchoring device 20 proximate the sutures 28. Sufficient deformation of the conductors (e.g., coils) can reduce efficacy or even result in complete failure (e.g., shorting) of the lead 22. The lead 22 can also sustain damage to the insulating sheath 26, for example if the sutures 28 cut through the anchoring device 20 and into the insulating sheath 26.

Figure 3:
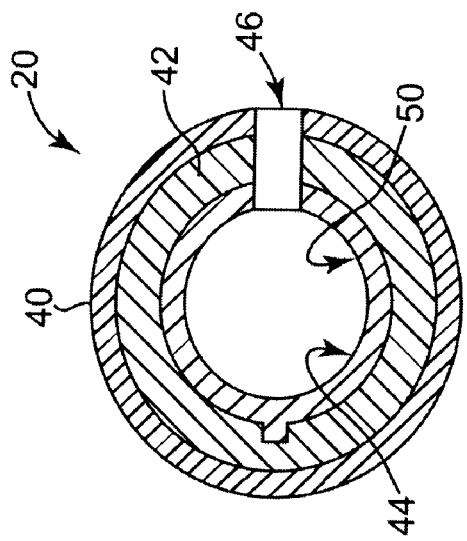
FIG. 3 shows a cross-section of the anchoring device of FIG. 2 in an open state taken along line 3-3 of FIG. 2.
Figure 2:
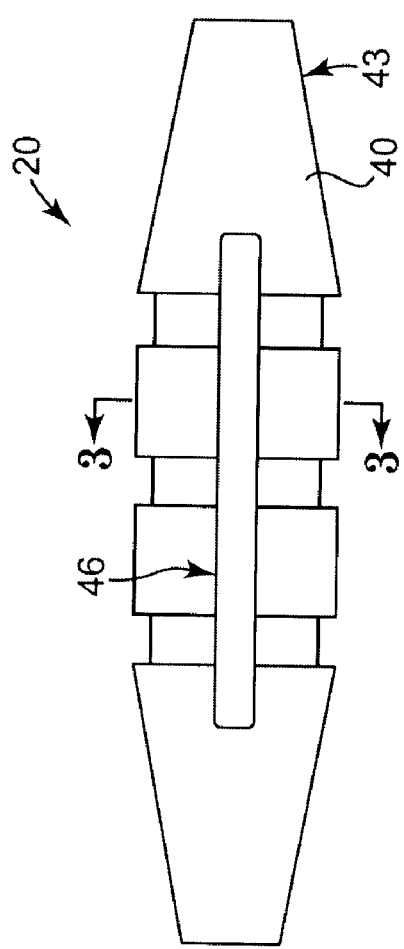
FIG. 2 is a front view of an anchoring device of the anchoring system of FIG. 1, according to some embodiments of the invention.

Various anchoring device embodiments are provided herein demonstrating features usable in the system 10 of FIG. 1. FIGS. 2-6 show various features of the anchoring device 20 suitable for use with the system 10 of FIG. 1, according to some embodiments. FIG. 2 is a front view of the anchoring device 20 while FIG. 3 shows a cross-section of the anchoring device 20 along line 3-3 of FIG. 2. As shown in FIGS. 2 and 3, the anchoring device 20 includes a sleeve 40 and a compression governor 42 (FIG. 3), which can also be described as a compression control collar. The anchoring device 20 is substantially elongate and tapers down in outer diameter at each end. The anchoring device 20 is adapted to coaxially receive the lead 22. As shown in FIG. 3, the governor 42 is embedded inside the sleeve 40.

The anchoring device 20 also optionally has at least one slot 46 formed through the anchoring device 20. The slot 46 extends in a longitudinal direction along a portion of the anchoring device 20 according to some embodiments. In other embodiments, the slot 46 extends along an entire length of the anchoring device 20. The slot 46 facilitates compression of the anchoring device 20 under the tying force of the sutures 28 (FIG. 1).

FIG. 4 is an isometric view of the sleeve 40. As shown in FIG. 4, the sleeve 40 generally helps to define the substantially elongate, hollow, tubular, and tapered form of the anchoring device 20. The sleeve 40 has a generally smooth inner bore 50 (FIG. 3), although roughening or other friction enhancing features are incorporated in some embodiments. The sleeve 40 also has an outer surface 52 with a plurality of circumferentially extending suture grooves 54 formed into the outer surface 52. A slot 56 extending in a longitudinal direction is also formed from the outer surface 52 to the inner bore 50 and extends lengthwise along a portion of the sleeve 40 to intersect the suture grooves 54. The sleeve 40 also optionally includes a plurality of through holes 55 to facilitate molding the sleeve 40 and the compression governor 42 together, for example.

In some embodiments, the inner bore 50 of the sleeve 40 defines an inner bore 44 of the anchoring device 20. Additionally, the sleeve 40 optionally forms an outer surface 43 (FIG. 2) of the anchoring device 20. According to various embodiments, the sleeve 40 is formed of an elastomeric material and is generally flexible, substantially compliant, and elastically compressible. In some embodiments, the sleeve 40 is formed of silicone or other biocompatible material having desired properties.

FIG. 5 shows a first portion 42a, or first segment 42a, of the compression governor 42. In various embodiments and as better shown in FIG. 6, the compression governor 42 includes a plurality of separate segments 42a, 42b, 42c. Each of the segments is optionally substantially similar. Thus, the segments 42a, 42b, 42c are described cumulatively with reference to the first segment 42a according to some embodiments.

Alternatively, the compression governor is a substantially monolithic, or unitary in structure with the various segments 42a, 42b, 42c being formed together as a single unit, although dividing the compression governor 42 into the segments 42a, 42b, 42c facilitates improved bendability of the anchoring device 20 along its longitudinal axis while retaining the compression control features of the anchoring device 20.

As shown in FIG. 5, the first segment 42a of the compression governor 42 defines an inner bore 60a and an outer surface 62a formed with a groove 64a which, upon assembly of the anchoring device 20, generally corresponds in shape and location to one of the plurality of suture grooves 54 of the sleeve 40 (FIG. 4). As shown in FIG. 5, the first segment 42a of the compression governor 42 defines a substantially C-shaped transverse cross-section. In particular, the first segment 42a of the compression governor 42 has a slot or gap 70a, extending in a longitudinal direction along the length of the first segment 42a.

The slot 70a is formed through the first segment 42a, from the outer surface 62a to the inner bore 60a. The first segment 42a of the compression governor 42 also defines first and second opposing edges 72a, 74a, respectively, along the longitudinally extending slot 70a. In some embodiments, the first segment 42a includes a hole 75a extending partially into the first segment 42a to facilitate molding/assembly to the sleeve 40, though the hole 75a additionally or alternatively serves other purposes.

The first segment 42a of the compression governor 42 is formed of a substantially more rigid material than the sleeve 40. For example, the first segment 42a of the compression governor 42 is optionally formed of PEEK, nickel-titanium alloys, polysulfone, polyurethane, a higher durometer silicone or other materials having suitable properties. Although formed to be more rigid, the first segment 42a of the compression governor 42 is adapted to be compressible or collapsible to a desired extent. In some embodiments, the first segment 42a of the compression governor 42 is biased to a natural position, or is otherwise spring-like in nature.

As shown in FIG. 5, the inner bore 60a of the first segment 42a also has a longitudinally, or axially, extending groove 76a formed into the inner bore 60a and positioned generally opposite the slot 70a. The groove 76a is optionally implemented to reduce the compressive force needed to compress, or dilate, the first segment 42a to a predetermined limit.

As shown in FIG. 6, each of the segments 42a, 42b, 42c of the compression governor 42 are coaxially received within the sleeve 40 with each aligned to a respective one of the suture grooves 54. As shown in FIG. 6, the longitudinally extending slots 56, 70 are aligned with one another to form the slot 46 of the anchoring device 20. In some embodiments, the sleeve 40 and compression governor 42 are molded together such that the compression governor 42 is substantially embedded within the sleeve 40. In particular, the inner bores 60 and outer surfaces 62 are substantially covered by the sleeve with the first and second edges 72, 74 being exposed as shown in FIG. 6 or covered (not shown) as desired.

As shown, the compliant material of the sleeve 40 covers a substantial portion of the inner bores 60 of the segments 42a, 42b, 42c. Thus, in some embodiments, there is compliant material forming portions of the inner bore 44 that will be compressed against the lead 22 (FIG. 1), as well as forming portions of the outer surface 46 of the anchoring device 20 that will receive the sutures 28.

In other embodiments, the compression governor 42 is only partially embedded into the sleeve 40 such that some or all of the inner bore and/or the outer surface of one or more of the segments 42a, 42b, 42c of the compression governor 42 are exposed. However, by having the compressible material at the inner bore 44, and thus at the lead-anchoring device interface under the suture grooves 54, there is better surface contact and increased friction between the lead 22 and anchoring device 20, according to some embodiments. In turn, having compressible material at the outer surface 46 can also help grip the sutures 28 to facilitate tying them about the device 20.

Figure 3A:
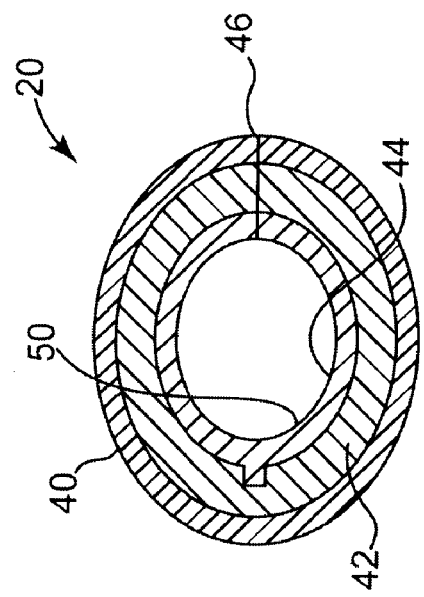
FIG. 3A shows a cross-section of the anchoring device of FIG. 3 in a closed, or compressed state.

The compression governor 42 is generally positioned under the suture grooves 54 of the sleeve 40 such that it operates to substantially limit compression of the anchoring device 20. In particular, upon application of an external compressive force (e.g., tying of the sutures 28 about the device 20) on each of the segments 42a, 42b, 42c, the longitudinally extending slots 70 are reduced in width from an initial, open state until the first and second opposing edges 72, 74 are brought into close proximity (or contact) such that the segments 42a, 42b, 42c in particular, and the compression governor 42 more generally, are in a closed, or compressed state (FIG. 3A). In the open state, the inner bore 60 has a substantially larger effective diameter than in the closed state. As the first and second opposing edges 72, 74 make contact, further compression of the segments 42a, 42b, 42c in particular, and the compression governor 42 in general, is substantially limited.

In some embodiments, compression of the anchoring device 20 is substantially limited, or controlled, by the compression governor 42 in that further compression would require plastic deformation or breaking of the compression governor 42. Compression can also be substantially limited in that there is a sharp increase in the force necessary to accomplish further compression as the various edges 72, 74 are abutted (either directly against one another or through interceding material of the sleeve 40). As still another example of compression control, compression can also be substantially limited in that a physician manually compressing the compression governor 42 is provided tactile or visual feedback that a limit, or stopping point, has been reached when the slot 46 of the anchoring device 20 is sufficiently compressed that the various first and second edges 72, 74 come into contact or otherwise interfere with further compression.

During use, the anchoring device 20 is coaxially received over the lead 22 and is slid to a desired location on the lead 22. In some embodiments, the anchoring device 20 is adapted to allow the anchoring device 20 to readily slide over the lead 22 when the compression governor 42 is in the open state.

The sutures 28 are aligned to the suture grooves 54 and tightened about the anchoring device 20 to secure the anchoring device to the lead 22 and the anchoring device to surrounding tissue of the patient's body 12. In some embodiments, the sutures 28 (FIG. 1) are secured proximate a vein entry site where the lead 22 enters vasculature of the patient. As the sutures 28 are tightened about the anchoring device 20, the anchoring device 20 is compressed, or collapsed, from the open state to the closed state, where the closed state includes the slot 46 closing onto itself and the effective diameter of the inner bore 60, and thus the effective inner diameter of the inner bore 50 of the sleeve 40, decreasing in size. In particular, the segments 42a, 42b, 42c are each compressed as the sutures 28 are each tied about a corresponding groove 54.

The inner bore 50 of the sleeve decreases in effective diameter as the device 20 is transitioned to the closed state. In some embodiments, the compressible material of the sleeve 40 is abutted against the lead 22 when the device 20 is in either the open state, or in a partially closed state, such that transition of the device 20 to the closed state results in compression of the sleeve material against the lead 22. Thus, in some embodiments, compression of the sleeve material can take up, or absorb, some or all of the reduction in effective diameter that the inner bore 50 of the sleeve would otherwise exhibit.

Upon closing the slot 46, the more rigid or less compliant material of the compression governor 42 limits, or otherwise inhibits further compression of the anchoring device 20 onto the lead 22. In particular, the compression governor 42 is compressible up to a pre-selected extent. For example, when the lead 22 is not disposed in the bore 44, the compression governor 42 in particular, and the device 20 more generally, is compressible up to a minimum effective diameter before further compression is limited. This limited allowable compression sets a threshold for compressive forces that are exerted on the lead 22 by the anchoring device 20 as the sutures 28 (FIG. 1) are tied about the device 20.

In particular, the first and second edges 72, 74 of the segments 42a, 42b, 42c of the compression governor 42 are either directly abutted against one another or are indirectly abutted by sufficiently pinching adjacent material (e.g., compliant material of the sleeve 40 residing between the edges 72, 74) to resist further compression of the anchoring device 20 onto the lead 22.

In some embodiments, the physician feels that the anchoring device 20 is in the closed state or is otherwise given tactile feedback that the limit has been reached, and is thereby informed to cease tightening the sutures 28. The closing of the slot 46 also optionally provides visual feedback that the limit has been reached upon the physician viewing that the slot 46 has closed. In some embodiments, the less compliant compression governor 42 also helps to spread out crushing forces that would otherwise be concentrated closely around each of the sutures 28. In particular, in the absence of the more rigid compression governor 42, the sleeve 40 could otherwise translate a more concentrated load from the sutures 28 to the lead 22 through the sleeve 40.

FIGS. 7-9 show another anchoring device 120 suitable for use with the system 10 of FIG. 1. The anchoring device 120 is optionally usable in a substantially similar manner, according to substantially similar methods, to the anchoring device 20 to secure the lead 22 within the patient's body 12. FIG. 7 shows the anchoring device 120 from a front view and FIG. 8 shows the anchoring device 120 from a cross-sectional view. As shown in FIGS. 7 and 8, the anchoring device 120 includes a sleeve 140 and a compression governor 142. The anchoring device 120 is substantially elongate with tapered ends, has an outer surface 143 and an inner bore 144 (FIG. 10) adapted to coaxially receive the lead 22, and also has a plurality of longitudinally extending slots 146 formed from the outer surface 143 to the inner bore 144 of the anchoring device 120.

As shown in FIG. 7, the sleeve 140 generally defines the substantially elongate, hollow, tubular, and tapered body of the device 120. As shown in FIG. 8, the sleeve 140 has a substantially smooth inner bore 150, although roughening or other friction enhancing features may be incorporated, and an outer surface 152 with a plurality of circumferentially extending suture grooves 154 formed into the outer surface 152. The sleeve 140 is formed of an elastomeric material and is substantially flexible, compliant, and elastically compressible.

The sleeve 140 has a plurality of longitudinally extending slots 156 formed from the outer surface 152 to the inner bore 150 that extend lengthwise along the sleeve 140 to intersect the suture grooves 154. In general terms, the slots 156 of the sleeve 140 facilitate compression of the anchoring device 120 under the tying force of the sutures 28. As with some of the other embodiments previously described, and as shown in FIG. 8, the inner bore 150 of the sleeve 140 defines the inner bore 144 of the anchoring device 120.

FIG. 9 shows the compression governor 142 from an isometric view. The compression governor 142 is substantially elongate, tubular, and hollow or barrel-shaped. The compression governor 142 defines an inner bore 160 and an outer surface 162. The compression governor 142 also has a plurality of longitudinally extending slots 170 and includes two opposing collars, or end portions 171 that the slots 170 extend between. The compression governor 142 also defines first and second opposing edges 172, 174 along each of the longitudinally extending slots 170. In particular, the slots 170 are formed through the compression governor 142 and disposed circumferentially about the compression governor 142.

FIG. 10 shows the anchoring device 120 in transverse cross-section along line 10-10 shown in FIG. 7. As shown in FIG. 10, the compression governor 142 is coaxially received with the sleeve 140. In some embodiments, the sleeve 140 is molded over the compression governor 142, such that the compression governor 142 is substantially embedded within the sleeve 140.

As shown in FIG. 10, the compliant material of the sleeve 140 covers the compression governor 142. Thus, as with some other embodiments, there is compliant material forming at least a portion of the inner bore 144 and the outer surface 143 of the anchoring device 120. As previously referenced, compressible material can help facilitate retention of the lead 22 and/or sutures 28 (FIG. 1) according to some embodiments. In other embodiments, the compression governor 142 is embedded into the inner bore 150 (FIG. 8) of the sleeve 140 such that the inner bore 160 (FIG. 9) of the compression governor 142 is exposed and the outer surface 162 (FIG. 9) of the compression governor 142 is covered by the sleeve 140. In still other embodiments, the compression governor 142 is disposed about the sleeve 140 or embedded into the outer surface 152 of the sleeve 140 such that the inner bore 160 of the compression governor 142 is covered while the outer surface 162 is exposed.

As shown in FIG. 10, with the anchoring device 120 in the assembled state, the pluralities of longitudinally extending slots 156, 170 are aligned within one another to combine to form the plurality of slots 146 of the anchoring device 120, although unaligned slots are also contemplated. As with some other embodiments, the compression governor 142 is positioned under the suture grooves 154 (FIG. 8) of the sleeve 140 to help ensure limiting and distribution of compression forces on the lead 22.

As previously described, the compression governor 142 is formed to be substantially more rigid than the sleeve 140. In general terms, the compression governor 142 is formed to be compressible or collapsible to a predetermined limit under an external force, where the predetermined limit is reached upon sufficient narrowing of the slots 170. More particularly, upon application of an external force, the longitudinally extending slots 170 are reduced in width from an initial, open state until the first and second opposing edges 172, 174 of the slots 170 contact, interfere, or otherwise resist further compression of the anchoring device 20 onto the lead 22 at a closed, or compressed state (not shown).

As the slots 170 are reduced in width, the inner bore 160 of the compression governor 142 approaches a predetermined minimum transverse cross-sectional area or a predetermined minimum effective diameter. The limiting effect of the compression governor 142 is translated to the sleeve 140 such that the inner bore 144 of the anchoring device 120 also approaches a predetermined minimum transverse cross-sectional area or a predetermined minimum effective diameter, although the presence of the lead 22 in the inner bore 144 can affect the amount of reduction in effective diameter of inner bore 144 as previously described.

In some embodiments, the edges 172, 174 of the compression governor 142 directly interfere with one another, or are abutted against one another. In other embodiments, some of the compressible material of the sleeve 140 resides within the slots 170, such that the compressible material is compressed between the opposing edges 172, 174 with increasing resistance until a limit is effectively reached.

Compression of the anchoring device 120 is substantially limited or controlled by the compression governor 142 in that further compression would require plastic deformation or breaking of the compression governor 142; there is a sharp increase in the force necessary to accomplish further compression as the edges 172, 174 of the compression governor 142 are abutted (either directly against one another or through an intermediate material), and/or a physician manually compressing the compression governor 142 is provided tactile and visual feedback that a limit, or stopping point, has been reached when the slots 146 of the device 120 are sufficiently compressed that the first and second edges 172, 174 come into contact or otherwise interfere with further compression.

In some embodiments, the less compliant compression governor 142 also helps to spread out crushing forces that would otherwise be concentrated closely around each of the sutures 28. In particular, in the absence of the more rigid compression governor 142, the sleeve 140 could otherwise translate a more concentrated load from the sutures 28 to the lead 22.

FIGS. 11-14 show another anchoring device 220 suitable for use in the anchoring system 10 of FIG. 1. The anchoring device 220 is optionally usable in a substantially similar manner, according to substantially similar methods as other embodiments to secure the lead 22 at a desired location within the patient's body 12.

FIG. 11 is a front view of the anchoring device 220 and FIG. 12 is a cross-sectional view of the anchoring device 220 along line 12-12 in FIG. 11. As shown in FIGS. 11 and 12, the anchoring device 220 includes a sleeve 240 and a compression governor 242. The anchoring device 220 is substantially elongate with tapered ends and has an outer surface 243 and an inner bore 244 adapted to coaxially receive the lead 22.

The sleeve 240 generally defines the substantially elongate, hollow, tubular, and tapered shape of the anchoring device 220 according to some embodiments. The sleeve 240 also has a substantially smooth inner bore 250, although roughening or other friction enhancing features are contemplated. The sleeve 240 also has an outer surface 252 with a plurality of circumferentially extending suture grooves 254 formed therein. The inner bore 250 is stepped with an increase in diameter to receive the compression governor 242 as subsequently described.

The sleeve 240 is optionally formed of an elastomeric material and is generally flexible, substantially compliant, and elastically compressible. The sleeve 240 is formed of silicone or other biocompatible material having suitable properties, such as those previously described.

Figure 13:
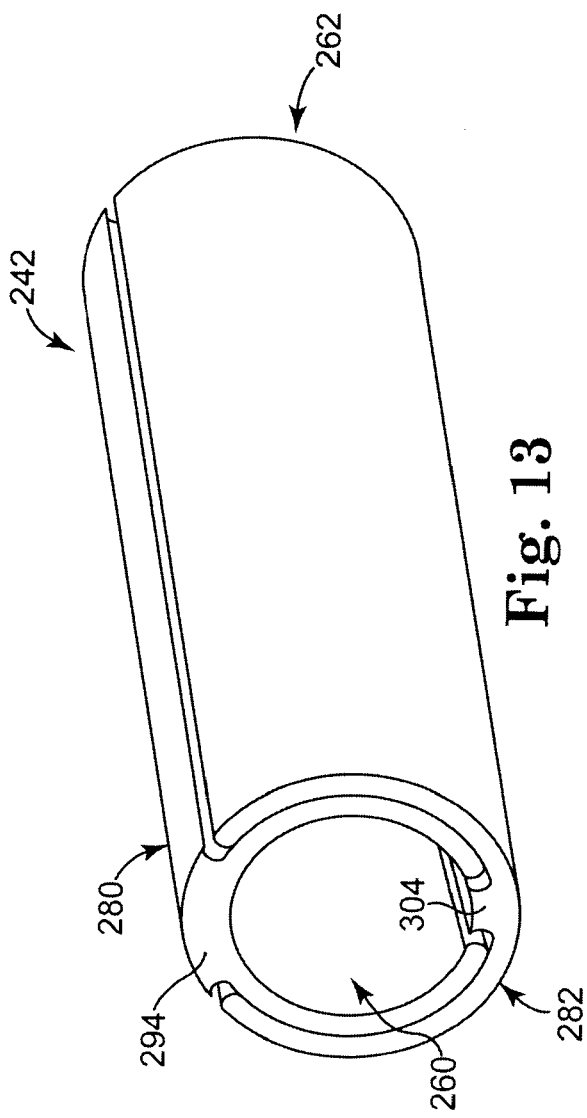
FIG. 13 is an isometric view of a compression governor of the anchoring device of FIG. 11.
Figure 14:
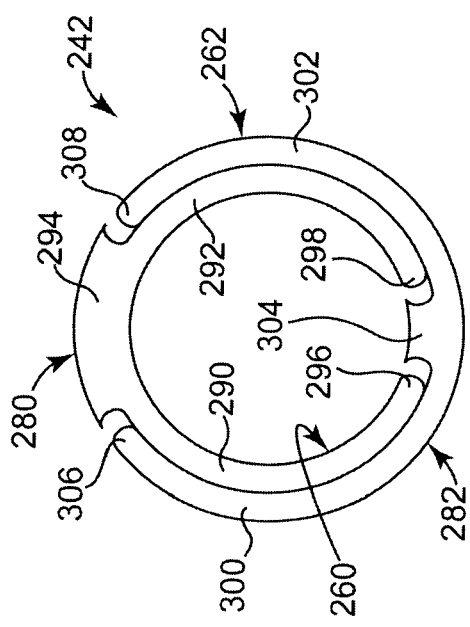
FIG. 14 is an end view of the compression governor of FIG. 13.

FIG. 13 is an isometric view of the compression governor 242 and FIG. 14 is an end view of the compression governor 242. As shown in FIGS. 13 and 14, the compression governor 242 defines an inner bore 260 and an outer surface 262 formed by the combination of a first member 280 and a second member 282 that work cooperatively to limit dilation, or compression, of the compression governor 242.

The first member 280 is substantially C-shaped, having first and second arms 290, 292 and a radially outwardly projecting stop feature 294. The first and second arms 290, 292 define ends 296, 298, respectively. In turn, the second member 282 is also substantially C-shaped with third and fourth arms 300, 302 and an inwardly projecting stop feature 304. The third and fourth arms 300, 302 also define ends 306, 308, respectively.

As shown in FIGS. 13 and 14, the first member 280 is coaxially received in the second member 282, with the first and second arms 290, 292 embraced between the third and fourth arms 300, 302. The first and second arms 290, 292 are each circumferentially slidable relative to the third and fourth arms 300, 302, such that the first and second arms 290, 292 are collapsible toward one another and the third and fourth arms 300, 302 are also collapsible toward one another.

In particular, upon application of a compressive force on the compression governor 242, the ends 296, 298 of the first and second arms 290, 292 slide toward, and eventually abut the inwardly projecting stop feature 304 of the second member 282. In turn, the ends 306, 308 of the second member 282 slide toward, and eventually abut the outwardly projecting stop feature 294 of the first member 280.

In general terms, the stop features 294, 304 provide means for limiting the maximum amount of compression that the compression governor 242 undergoes under an external force. More specifically, as the stops 294, 304 are abutted, the inner bore 260 of the compression governor 142 approaches a predetermined minimum transverse cross-sectional area or a predetermined minimum effective diameter. In some embodiments, the initial spacing between the ends 296, 298 and the stop feature 304, as well as the initial spacing between the ends 306, 308 and the stop feature 294 are selected according to a desired amount of travel, or amount of dilation that the compression governor 242 undergoes as it transitions between open and closed states (note the closed state is not shown).

As shown in FIG. 12, the compression governor 242 is coaxially received with the sleeve 240. As with some other embodiments the compression governor 242 is positioned under the suture grooves 254 of the sleeve 240. In some embodiments, the sleeve 240 is molded over the compression governor 242, such that the compression governor 242 is substantially embedded within the sleeve 240. As shown in FIG. 12, the compression governor 242 is partially embedded into the inner bore 250 of the sleeve 240 such that the inner bore 260 is exposed and the outer surface 262 of the compression governor 242 is covered by the sleeve 240. In other embodiments, the compression governor 242 is disposed about the sleeve 240 or embedded into the outer surface 252 of the sleeve 240 such that the inner bore 260 of the compression governor 242 is covered while the outer surface 262 is exposed.

As described in association with some other embodiments, compression of the anchoring device 220 is substantially limited or controlled by the compression governor 242 in that further compression would require plastic deformation or breaking of the compression governor 242; a sharp increase in force is necessary to accomplish further compression as the edges 272, 274 of the compression governor 242 are abutted (either directly against one another or through an intermediate material); and/or a physician manually compressing the compression governor 242 is provided tactile feedback and/or visual feedback (when slots or other indicators are visible) that a limit, or stopping point, has been reached when the device 220 is sufficiently compressed that the ends 296, 298, 306, 308 and stop features 304, 294, respectively, come into contact or otherwise inhibit further compression.

In some embodiments, the less compliant compression governor 242 also helps to spread out crushing forces that would otherwise be concentrated closely around each of the sutures 28. In particular, in the absence of the more rigid compression governor 242, the sleeve 240 could otherwise translate a more concentrated load from the sutures 28 to the lead 22.

FIGS. 15-20 show another anchoring device 420 suitable for use with the system 10 of FIG. 1, according to some embodiments, where the anchoring device 420 is optionally usable in a substantially similar manner, according to substantially similar methods, to the anchoring device 20 to secure the lead 22 within the patient's body 12. As shown in FIG. 15, the anchoring device 420 includes a sleeve 440 and a compression governor 442 received coaxially about the sleeve 440. In general terms, the anchoring device 420 is substantially elongate and tapers down in outer diameter at each end. The anchoring device 420 has an inner bore 444 (FIG. 19) adapted to coaxially receive the lead 22, where the compression governor 442 of the anchoring device 420 acts to limit the compressive forces applied to the lead 22 (FIG. 1).

FIG. 16 is a cross-sectional view of the sleeve 440 taken along line 16-16 of FIG. 15. As shown in FIG. 16, the sleeve 440 generally helps to define the substantially elongate, hollow, tubular, and tapered form of the anchoring device 420 (FIG. 15). The sleeve 440 has a substantially smooth inner bore 450 with a reduced diameter portion 451 for enhancing friction between the lead 22 (FIG. 1) and the sleeve 440. In some embodiments, and as shown in FIG. 19, the inner bore 450 of the sleeve 440 defines the inner bore 444 of the anchoring device 20.

The sleeve 440 also has an outer surface 452 forming a recessed area 454 located toward the center of the sleeve 440 and extending about the circumference of the sleeve 440. The recessed area 454 is adapted to receive the compression governor 442 (FIG. 18). The sleeve 440 is formed of an elastomeric material and is generally flexible, substantially compliant, and elastically compressible. In some embodiments, the sleeve 440 is formed of silicone or other biocompatible material having desired properties.

FIG. 17 is a top view of the compression governor 442. As shown in FIG. 17, the compression governor 442 is substantially elongate, tubular, and hollow, or barrel-shaped. In some embodiments, the compression governor 442 defines an inner bore 460 (FIG. 18) and an outer surface 462 formed with a plurality of circumferentially extending suture grooves 464 adapted to receive the sutures 28 (FIG. 1). The compression governor 442 also includes a plurality of transversely extending slots, or windows 470 formed at least partially within each of the plurality of suture grooves 464. The windows 470 extend through a thickness of the compression governor 442, from the outer surface 462 to the inner bore 460.

FIG. 18 is a cross-section of the compression governor 442 taken along line 18-18 of FIG. 17. As shown in FIG. 18, the windows 470 include a first set of windows 470a positioned at the top of the compression governor 442 and a second set of windows 470b positioned at the bottom of the compression governor 442, opposite the first set of windows 470a.

The compression governor 442 is formed of a substantially more rigid material than the sleeve 440. In some embodiments, the compression governor 442 is substantially incompressible under loading conditions associated with tying one of the sutures 28 or other fastening means about the anchoring device 420. For example, the compression governor 442 is optionally formed of PEEK, nickel-titanium alloys, polysulfone, polyurethane, silicone of a higher durometer or other materials having suitable properties.

Additionally, although the compression governor 442 is shown as a substantially monolithic, or unitary structure formed as a single piece, in various embodiments the compression governor 442 is segmented, or otherwise broken into a plurality of segments (not shown). In particular, the compression governor 442 is optionally segmented along the longitudinal axis to facilitate bending the anchoring device 420 while retaining the compression control features of the device 420.

FIGS. 19 and 20 are transverse cross-sections of the anchoring device 420 along line 19-19 of FIG. 18. As shown in FIG. 15 and FIG. 19, upon assembly of the anchoring device 420, the compression governor 442 is coaxially secured to the sleeve 440 with the compression governor 442 received in the recessed area 454 (FIG. 16) of the sleeve 440. One or more portions 456 of the sleeve 440 protrude radially outward from the windows 470 in the compression governor 442. The portions 456 are exposed through the windows 470 and are aligned with the suture grooves 464 (FIG. 17) of the compression governor 462. As will be described in greater detail, the portions 456 of the sleeve 440 are able to be depressed into the windows 470 to reduce the effective diameter of the inner bore 450 of the sleeve 440.

In particular, FIG. 19 shows the anchoring device 420 in a substantially relaxed, or natural state, also described as a non-compressed state. The non-compressed state includes the portions 456 protruding from the windows 470 and not otherwise being depressed into the windows 470.

FIG. 20 shows the anchoring device 420 in a compressed state (without the lead 22 received therein). As shown in FIG. 20, one of the sutures 28 has been tied about the anchoring device 420 in one of the suture grooves 464 (FIG. 17). In particular, the anchoring device 420 is adapted such that the sutures 28 are able to inwardly compress the portions 456 of the sleeve 440 into the windows 470, which, in turn, compresses the sleeve 440 to reduce the effective diameter of the inner bore 450.

When the lead 22 is present within the inner bore 450 (not shown), compressing the sleeve 440 radially inward results in a compression force, and thus an increase in retention force, between the anchoring device 420, and in particular the sleeve 440, and the lead 22.

The compression governor 442 is adapted to limit the compressive force on the lead once the sutures 28 extend substantially straight across the windows 470 as shown in FIG. 20. In particular, further tightening of the sutures 28 would require substantial deformation of the compression governor 442, which, as previously referenced, is formed to be substantially less compressible than the sleeve 440, as well as substantially incompressible under suture tying forces according to some embodiments. Thus, where the lead 22 is received in the inner bore 450, tightening the sutures 28 until they are straight effectively limits the amount of compressive forces translated to the lead 22. The physician is also provided a visual indicator that the limit has been reached upon the physician (or other user) noting that the sutures 28 are extending substantially straight across the windows 470.

As with some other embodiments described herein, the anchoring device 420 is adapted to substantially limit or control compressive forces in that further compression would require plastic deformation or breaking of the compression governor 442; there is a sharp increase in the force necessary to accomplish further compression of the compression governor 442 results at the limit; and/or a physician manually compressing the compression governor 442 is provided tactile feedback and/or visual feedback that a limit, or stopping point, has been reached when the sutures 28 extend straight across the windows 470.

FIGS. 21-25 show another anchoring device 520 suitable for use with the system 10 of FIG. 1, according to some embodiments, where the anchoring device 520 is optionally usable in a substantially similar manner, according to substantially similar methods, to other embodiments. As shown in FIG. 21, the anchoring device 520 includes a sleeve 540 and a compression governor 542 received coaxially about the sleeve 540. In general terms, the anchoring device 520 is substantially elongate and tapers down in outer diameter at each end. The anchoring device 520 is adapted to coaxially receive the lead 22 (FIG. 1) in an inner bore 544 (FIG. 26), where the compression governor 542 of the anchoring device 520 acts to limit the compressive forces applied to the lead 22 by the anchoring device 520.

FIG. 22 is a cross-sectional view of the sleeve 540 taken along line 22-22 of FIG. 21. As shown in FIG. 22, the sleeve 540 generally defines the substantially elongate, hollow, tubular, and tapered form of the anchoring device 520. The sleeve 540 has an inner bore 550 with a reduced diameter portion 551 for enhancing friction between the lead 22 (FIG. 1) and sleeve 540. In particular, the inner bore 550 of the sleeve 540 defines the inner bore 544 (FIG. 24) of the anchoring device 520, which, in turn, coaxially receives the lead 22.

The sleeve 540 also has an outer surface 552 forming a recessed area 554 toward the center of the sleeve 540 and extending about the circumference of the sleeve 540. The recessed area 554 is adapted to coaxially receive the compression governor 542. The sleeve 540 is formed of an elastomeric material and is generally flexible, substantially compliant, and elastically compressible. In some embodiments, the sleeve 540 is formed of silicone or other biocompatible material having desired properties.

FIG. 23 is a top view of the compression governor 542. As shown in FIG. 23, the compression governor 542 is substantially elongate, tubular, and hollow, or barrel-shaped. The compression governor 542 is formed of a substantially more rigid material than the sleeve 540. For example, the compression governor 542 is optionally formed of PEEK, nickel-titanium alloys, polysulfone, polyurethane, silicone of a higher durometer or other materials having suitable properties.

Although the compression governor 542 is shown as a substantially monolithic, or unitary structure formed as a single piece, in various embodiments the compression governor 542 is segmented, or otherwise broken into a plurality of segments (not shown) as described in association with other embodiments.

In some embodiments, the compression governor 542 defines an inner bore 560 (FIG. 24) and an outer surface 562 formed with a plurality of circumferentially extending suture grooves 564 adapted to receive the sutures 28 (FIG. 1). The compression governor 542 also defines a length, a first end 566, and a second end 568 opposite the first end 566.

As shown, the compression governor 542 has a plurality of windows or slots 570, extending longitudinally inwardly from each of the opposite ends 566, 568. The plurality of longitudinally extending windows 570 are formed at least partially within each of the plurality of suture grooves 564. Each of the windows 570 extends partially along the length of the compression governor 542, extending from one of the ends 566, 568 and terminating prior to reaching the opposite end. In some embodiments, each of the windows 570 defines a first edge 572 and a second edge 574 and extends about half way along the compression governor 542.

As shown, the windows 570 at each of the ends 566, 568 are staggered relative to one another. For example, in some embodiments, the windows 570 are configured with a first set 570a of the windows 570 extending from the first end 566 and a second set 570b of the windows 570 extending from the second end 568 of the compression governor 542.

FIGS. 24 and 25 are cross-sectional views taken along line 24-24 of FIG. 21. FIG. 24 shows the device 520 in an open, or non-compressed state while FIG. 25 shows the device 520 in a compressed, or closed state. As shown in FIG. 24, the windows 570 extend through a thickness of the compression governor 542, from the outer surface 562 to the inner bore 560. Each of the windows 570 of the first set 570a is staggered circumferentially about the compression governor 542 at about ninety degree offsets, although a variety of angular offsets are contemplated. The second set 570b (shown in dotted lines in FIG. 24) is also staggered circumferentially about the compression governor 542 at about ninety degree offsets, although a variety of angular offsets are contemplated.

In some embodiments, and as shown in FIG. 24, the first set 570a is offset relative to the second set 570b by about forty-five degrees, although a variety of angular offsets are contemplated, such that the first and second sets 570a, 570b define an interleaved configuration with the two sets 570a, 570b being misaligned longitudinally. Although two sets of four windows are shown having the offsets described, various numbers of windows and angular offsets are contemplated.

Upon assembly, and as shown in FIG. 24, the compression governor 542 is coaxially received over the sleeve 540 such that there is compliant material forming at least a portion of the inner bore 544 of the anchoring device 520. The compressible material of the sleeve 540 at the inner bore 544, and thus at the lead-anchoring device interface, facilitates surface contact and frictional characteristics between the lead 22 and anchoring device 520, although a variety of configurations are contemplated.

In operation, upon application of an external compressive force (e.g., upon tying of the sutures 28 about the sutures grooves 564), the windows 570 are reduced in width from an initial, open state to the closed state of FIG. 25. The open states includes the inner bore 560 having a substantially larger effective diameter than in the closed state. As the sutures 28 are tightened, the first and second opposing edges 572, 574 are brought into close proximity such that the compression governor 542 is in the closed state.

Although not shown, it should be understood that upon disposing the lead 22 within the lumen 560, the device 520 applies increased compressive forces, and thus retention forces, on the lead 22 as the anchoring device 520 generally, and the compression governor 542 specifically, is transitioned to the closed state.

In some embodiments, the opposing edges 572, 574 contact toward the ends 566, 568 (FIG. 23) when the device 520 is in the closed state, while other more centrally located portions of the edges 572, 574 still define some gap. In other embodiments, the windows 570 are closed along substantially all of their lengths. As the windows 570 are closed, the inner bore 560 is reduced in effective diameter, which, in turn, applies a compressive force on the sleeve 640. The compressive force on the sleeve 540 results in a reduction in effective diameter of the inner bore 550 of the sleeve 540 and/or translation of a compressive force onto the lead 22 when the lead 22 is received in the anchoring device 520 (not shown).

As the first and second opposing edges 572, 574 pinch together, or in other terms, as the windows 570 are closed, further compression of the compression governor 542 is limited. As with other embodiments, where the compression governor 542 is spring-like in nature, the compression governor 542 can be biased to the closed or open states, although having the relaxed, natural state of the compression governor 542 be the open state can help facilitate sliding of the anchoring device 520 over the lead 22.

In view of the foregoing, compression of the anchoring device 520 is substantially limited, or in alternate terms controlled, by the compression governor 542 in that further compression beyond the closed state would require plastic deformation or breaking of the compression governor 542 once the edges 572, 574 are substantially abutted (either directly against one another or through an intermediate material); there is a sharp increase in the force necessary to accomplish further compression once the edges 572, 574 of the compression governor 542 are substantially abutted; and a physician manually compressing the compression governor 542 is provided tactile feedback that a limit, or stopping point, has been reached when the windows 570 are sufficiently compressed that the first and second edges 572, 574 are substantially abutted to interfere with further compression.

Additionally, In some embodiments, the less compliant compression governor 542 also helps to spread out crushing forces that would otherwise be concentrated closely around each of the sutures 28. In particular, in the absence of the more rigid compression governor 542, the sleeve 540 could otherwise translate a more concentrated load from the sutures 28 to the lead 22.

As still another example of compression control, a physician is provided a visual indicator that a limit, or stopping point, has been reached upon viewing that the windows 570 have been closed toward the ends 566, 568 or along a greater portion of their lengths. In some embodiments, the sleeve 540 and compression governor 542 are formed of differently colored materials to enhance an ability to see whether the windows 570 have been closed. For example, portions of the sleeve 540 under the windows 570 may be brightly colored so that their obfuscation upon closing the windows 570 is more apparent.

Figure 26:
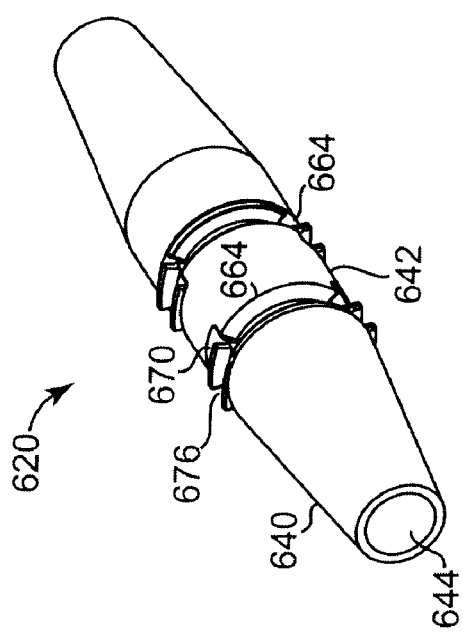
FIG. 26 is an isometric view of another anchoring device suitable for use with the anchoring system of FIG. 1, according to some embodiments of the invention.

FIGS. 26-32 show another anchoring device 620 suitable for use with the system 10 (FIG. 1) according to some embodiments, where the anchoring device 620 is optionally usable in a substantially similar manner, according to substantially similar methods, to the anchoring device 20 to secure the lead 22 within the patient's body 12. As shown in FIG. 26, the anchoring device 620 includes a sleeve 640 and a compression governor 642 received coaxially about the sleeve 640. In general terms, the anchoring device 620 is substantially elongate and tapers down in outer diameter at each end. The anchoring device 620 includes an inner bore 644 adapted to coaxially receive the lead 22 (FIG. 1), where the compression governor 642 of the anchoring device 620 acts to limit the compressive forces applied to the lead 22 by the anchoring device 620.

Figure 27:
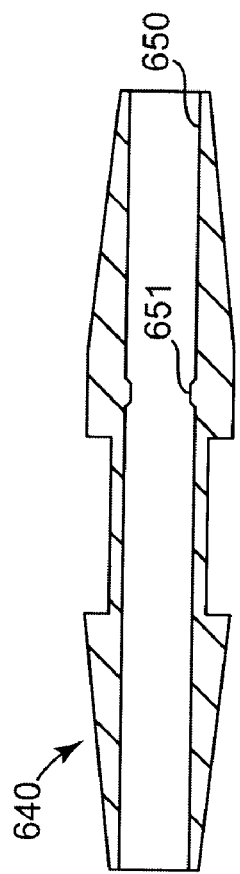
FIG. 27 shows a cross-section of a sleeve of the anchoring device of FIG. 26 taken along the central longitudinal axis of the sleeve.

FIG. 27 is a cross-sectional view of the sleeve 640 taken along the central longitudinal axis of the anchoring device 620. As shown in FIG. 27, the sleeve 640 generally helps to define a substantially elongate, hollow, tubular, and tapered form of the anchoring device 620. The sleeve 640 has an inner bore 650 with a reduced diameter portion 651 for enhancing friction between the lead 22 (FIG. 1) and sleeve 640. In particular, and as shown in FIG. 27, the inner bore 650 of the sleeve 640 defines the inner bore 644 of the anchoring device 620, which coaxially receives the lead 22.

The sleeve 640 also has an outer surface 652 forming a recessed area 654 about the circumference of the sleeve 640 that is adapted to coaxially receive the compression governor 642. The sleeve 640 is formed of an elastomeric material and is generally flexible, substantially compliant, and elastically compressible. In some embodiments, the sleeve 640 is formed of silicone or other biocompatible material having desired properties.

Figure 29:
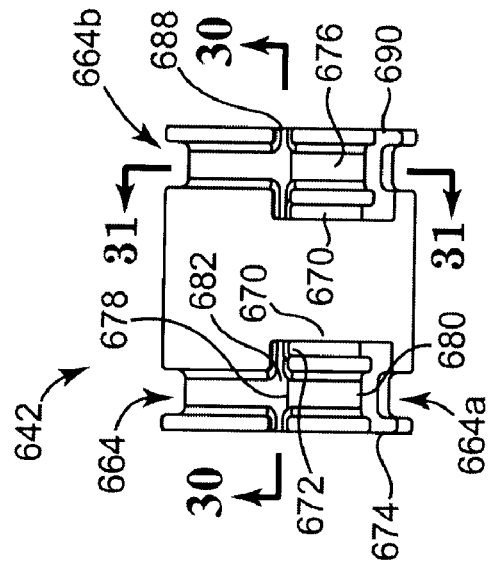
FIG. 29 is a top view of the compression governor of FIG. 28.
Figure 28:
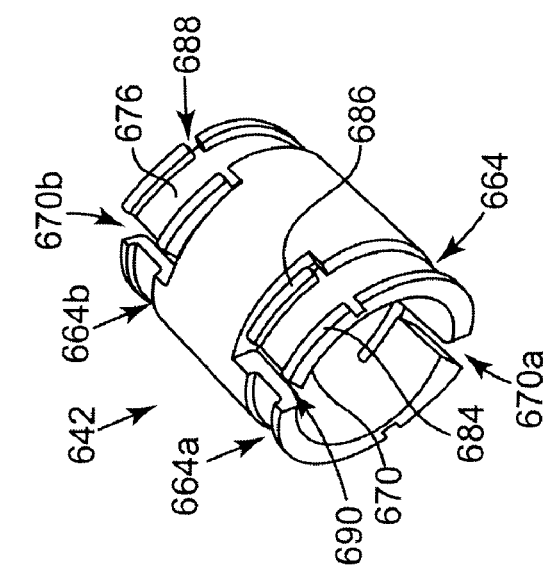
FIG. 28 is an isometric view of a compression governor of the anchoring device of FIG. 26.

FIG. 28 is an isometric view of the compression governor 642 and FIG. 29 is a top view of the compression governor 642. As shown in FIGS. 28 and 29, the compression governor 642 is substantially elongate, tubular, and hollow, or barrel-shaped. The compression governor 642 is formed of a substantially more rigid material than the sleeve 640. For example, the compression governor 642 is optionally formed of the materials previously referenced in association with other embodiments or other materials having suitable properties.

Although the compression governor 642 is shown as a substantially monolithic, or unitary structure formed as a single piece, in various embodiments the compression governor 642 is segmented, or otherwise broken into a plurality of segments (not shown). In particular, the compression governor 642 is optionally segmented along the longitudinal axis thereof to facilitate bending the anchoring device 620 along its longitudinal axis while retaining the compression control features of the anchoring device 620.

Figure 30:
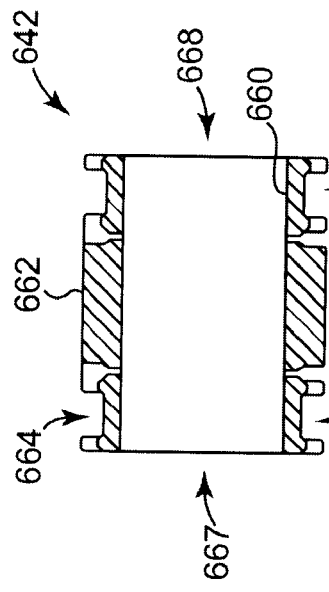
FIG. 30 shows a cross-section of the compression governor of FIG. 29 taken along line 30-30 of FIG. 29.

FIG. 30 is a cross-sectional view of the compression governor 642 taken along line 30-30 of FIG. 29. As shown, the compression governor 642 defines an inner bore 660 and an outer surface 662 formed with a plurality of circumferentially extending suture grooves 664 adapted to receive the sutures 28 (FIG. 1). The compression governor 642 also defines a length, a first end 667, and a second end 668 opposite the first end 667.

As shown in FIGS. 28 and 29, the compression governor 642 has a first suture groove 664a toward the first end 667 and a second suture groove 664b toward the second end 668 of the compression governor 642. The compression governor 642 also has a plurality of windows 670, also described as slots 670. Each of the plurality of windows 670 are substantially elongate in a circumferential direction. The compression governor includes a first pair of circumferentially-opposed windows 670a formed at the first end 667 and a second pair of circumferentially-opposed windows 670b formed at the second end 668.

The first pair of windows 670a at least partially intersect, or are at least partially positioned within, the first suture groove 664a, while the second pair of windows 670b are positioned at least partially within the second suture groove 664b. Each of the windows 670 defines a first edge 672 and a second edge 674 opposite the first edge 672.

The compression governor 642 also forms a plurality of flexible arms 676, including a first pair of circumferentially-opposed arms 676a and a second pair of circumferentially-opposed arms 676b. The flexible arms 676 each define first ends 678 and second ends 680. Each of the arms 676 forms first and second shoulders 684, 686 which correspond generally to the edges of the suture grooves 664. Each first end 678 extends from, and is continuously formed with, a corresponding first edge 672 of one of the windows 670 to define a living hinge 682, or is otherwise hingedly attached to one of the first edges 672.

In turn, each of the second ends 680 are free edges. As shown, each of the arms 676 defines a gap 688 in the shoulders 684, 686 at the first end 678 to facilitate flexing of the arms 676 at their hinges 682. A gap 690 is also defined between each of the second ends 680 of the arms 676 and the second edges 674 of the windows 670. As alluded to above, and as subsequently described in greater detail, the arms 676 are generally adapted to be flexed inwardly and outwardly within the windows 670.

Figure 32:
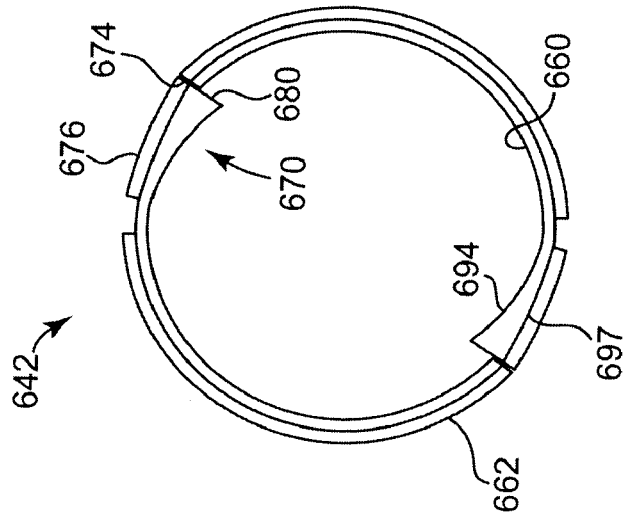
FIGS. 31 and 32 show a transverse cross-sectional view of the compression governor of FIG. 29 taken along line 31-31 of FIG. 29.
Figure 31:
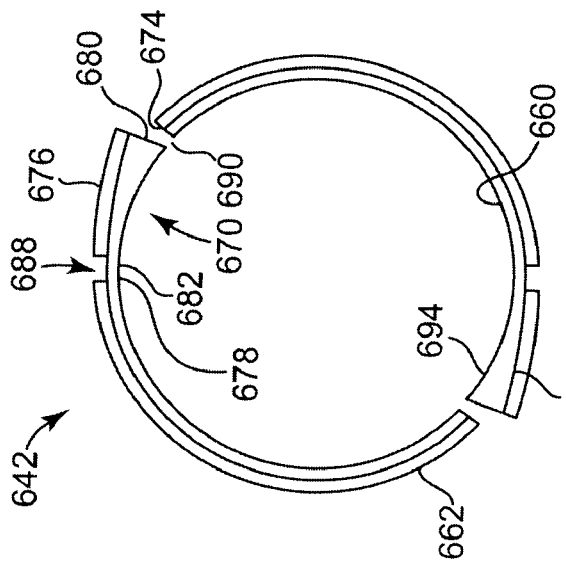

FIGS. 31 and 32 show a transverse cross-sectional view of the compression governor 642 taken along line 31-31 of FIG. 29. As described in greater detail, FIG. 31 shows the compression governor 642 in an open, non-compressed state while FIG. 32 shows the compression governor 642 in a closed, compressed state. As shown in FIGS. 31 and 32, the arms 676 each define an outer face 692 and an inner face 694 and a thickness between the outer and inner faces 692, 694. In some embodiments, the thicknesses of the arms 676 increase moving toward the second ends 680.

As shown in FIG. 31 (non-compressed state), the arms 676 are adapted such that the inner faces 694 define a substantially continuous, circular profile of the inner bore 660 in combination with a remainder of the compression governor 642. In turn, the outer faces 692 project outwardly, for example in a somewhat tangential direction, relative to the surrounding outer surface 662 of the compression governor 642.

As shown in FIG. 32, the closed, or compressed state includes the arms 676 being depressed into the windows 670 (more easily seen in FIG. 29). The inner faces 694 project inwardly to define a reduced effective inner diameter of the compression governor 642 relative to the non-compressed state. In some embodiments, the compressed state includes the outer faces 692 extending substantially straight across the windows 670 as subsequently described. In some embodiments, other than the flexible arms 676, the compression governor 642 is generally substantially incompressible under loading conditions associated with tying one of the sutures 28 (FIG. 1) or other fastening means about the anchoring device 620.

In an assembled state, as shown in FIG. 26, for example, the compression governor 642 is coaxially received about the sleeve 640 and is seated within the recessed area 654 (FIG. 27) of the sleeve 640. In operation, tying and tensioning the sutures 28 about the suture grooves 664 causes the arms to be flexed, depressed, or otherwise driven radially inward against the underlying sleeve 640 thereby reducing the effective inner diameter of the sleeve 640. When the lead 22 is disposed in the anchoring device 620, depression of the arms 676 into the windows 670 increases compressive forces between the sleeve 640 and lead 22, which, in turn, increases a retention force between the sleeve 640 and lead 22.

In some embodiments, the arms 676 are depressed until the sutures 28 (not shown in FIG. 32) extend over the outer faces 692 (FIG. 31) of the arms 676 along a substantially straight path over the windows 670. At that point, further depression of the arms 676 requires deformation of the compression governor 642. As such, the compression governor 642 limits, or controls, compressive forces on the lead 22 when the sutures 28 extend substantially straight across the windows 670.

In other embodiments, the gaps 690 (FIG. 31) between the arms 676 and the windows 670 are selected such that depression of the arms 676 into the windows 670 is limited at a preselected amount of depression. In particular, the gaps 690 are eventually closed when the second ends 680 (FIG. 31) of the arms 676 abut the second edges 674 (FIG. 31) of the windows 670 stopping further flexing of the arms 676. In this manner, the anchoring device 620 is adapted to be compressed to a predetermined limit upon tying of the sutures 28 (FIG. 1), which, in turn, limits or controls the compressive forces applied on the lead 22 by the anchoring device 620.

In view of the foregoing, compression of the anchoring device 620 is substantially limited, or in alternate terms controlled, by the compression governor 642 in that further compression beyond the closed state would require plastic deformation or breaking of the compression governor 642 once the sutures 28 extend substantially straight across the windows 670 and/or once the gaps 690 have been substantially closed; there is a sharp increase in the force necessary to accomplish further compression once the limit has been reached; and a physician manually compressing the compression governor 642 is provided tactile feedback that a limit, or stopping point, has been reached when the gaps 690 are closed and/or when the sutures 28 extend substantially straight across the windows 670.

As still another example of compression control, a physician is provided a visual indicator that a limit, or stopping point, has been reached upon viewing that the windows gaps 690 have been closed and/or that the sutures 28 extend substantially straight across the windows 670. Furthermore, similarly to some embodiments previously described, the sleeve 640 and compression governor 642 are optionally formed of differently colored materials to enhance an ability to see whether the gaps 690 have been closed.

Additionally, in some embodiments, the less compliant compression governor 642 also helps to spread out crushing forces that would otherwise be concentrated closely around each of the sutures 28. In particular, in the absence of the more rigid compression governor 642, the sleeve 640 could otherwise translate a more concentrated load from the sutures 28 to the lead 22.

Various embodiments of the anchoring device are characterized by one or more of a predetermined maximum compressive force to be applied to a lead, providing tactile feedback that such a limit has been reached, serving to distribute otherwise concentrated crushing forces across a broader area, accommodating sliding along the length of the lead prior to suture tie down when the anchoring device is in an open state, and allowing sufficient compressive force to be exerted on leads to stabilize them axially after tie down, as well as other additional or alternate features as desired.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical system comprising:
a medical lead;
an anchoring device received coaxially over the medical lead, the anchoring device including:
an elastomeric sleeve having a substantially elongate, hollow, and tubular body, the elastomeric sleeve extending a length of the anchoring device; and
a compression governor coaxially secured about the elastomeric sleeve, the compression governor adapted to limit compressive forces exerted on the lead by the anchoring device at a predetermined limit and provide a visual indicator that the predetermined limit has been reached as a result of the compression governor being compressed, wherein the compression governor has at least one window formed into the compression governor and the compression governor includes at least one flexible arm extending over the window and adapted to be flexed downwardly into the window to compress the sleeve; and
at least one fastener secured circumferentially about the anchoring device to cause the anchoring device to be compressed on the medical lead.

2. The system of claim 1, wherein the compression governor has:
a plurality of fastener grooves; and
a plurality of windows formed in the compression governor and positioned at least partially in the fastener grooves;
wherein the elastomeric sleeve protrudes radially outward from the plurality of windows in the compression governor.

3. The system of claim 2, wherein the visual indicator includes the fastener extending substantially straight across at least one of the plurality of windows.

4. The system of claim 1, wherein the visual indicator includes the fastener extending substantially straight across the window.

5. The system of claim 1, wherein the flexible arm defines a substantially flat top surface and the visual indicator includes the substantially flat top surface of the flexible arm extending substantially straight across the window.

6. The system of claim 1, wherein the compression governor defines a thickness, opposing ends, and a length, and further wherein the compression governor has at least one slot formed through a thickness of the compression governor extending from one of the ends of the compression governor partially along the length the compression governor.

7. The system of claim 6, wherein the visual indicator includes the slot being substantially closed.

8. An anchoring device for anchoring a medical lead implanted in a patient, the anchoring device comprising:
a sleeve having an elongate, hollow, and tubular shape, the sleeve further having an outer surface with at least one circumferential recessed area formed therein and a central bore adapted to slidably receive the medical lead;
a compression governor that is coaxially fitted about the sleeve in the recessed area and substantially less compliant than the sleeve, the compression governor having an outer surface, at least one circumferentially disposed groove formed partially into the outer surface, and at least one window in the compression governor positioned at least partially in the groove, wherein the window is defined by a first edge and a second edge of the compression governor and the compression governor further includes a flexible arm extending across the window, the flexible arm having a first end secured at a first edge of the window and a second end that is substantially free end.

9. The anchoring device of claim 8, wherein the compression governor defines a length and opposite ends and the window extends substantially longitudinally from one of the ends partially along the length of the compression governor.

10. The anchoring device of claim 8, wherein the flexible arm defines a first position and a second position, the second position including the flexible arm compressing the sleeve more than when the flexible arm is in the first position.

11. The anchoring device of claim 10, wherein the flexible arm defines a substantially flat top surface, and further wherein the flexible substantially flat top surface extends substantially straight across the window when the arm is in the second position.

12. The anchoring device of claim 8, wherein the sleeve includes at least one portion that extends radially outward from the window of the compression governor.

13. A method of limiting compression of an anchoring device on a medical lead, the method comprising:
coaxially receiving a medical lead within the anchoring device, the anchoring device having a groove for receiving a fastener and comprising:
a sleeve having an elongate, hollow, and tubular shape, and a bore for receiving the lead, the sleeve having an outer surface with at least one circumferential recessed area formed therein;
a compression governor that is coaxially fitted about the sleeve in the recessed area and that is substantially less compliant than the sleeve, the compression governor having a window through the sleeve and being adapted to limit compressive force on the lead to a predetermined maximum compressive force, wherein the compression governor includes a flexible arm extending over the window and providing a visual indicator that the maximum compressive force has been reached with the window of the compressive sleeve includes causing the flexible arm to depress into the window with the fastener;
tying a fastener about the groove to compress the anchoring device onto the lead with the maximum compressive force; and
providing a visual indicator that the maximum compressive force has been reached using the window of the compressive sleeve.

14. The method of claim 13, wherein providing a visual indicator that the maximum compressive force has been reached with the window of the compressive sleeve includes causing the fastener to extend substantially straight across the window.

15. The method of claim 13, wherein providing a visual indicator that the maximum compressive force has been reached with the window of the compressive sleeve includes causing the window to substantially close with the fastener.

16. The method of claim 13, wherein the compression governor includes a flexible arm extending over the window and providing a visual indicator that the maximum compressive force has been reached with the window of the compressive sleeve includes causing a substantially flat top surface of the flexible arm to extend substantially straight across the window using the fastener.

17. The method of claim 13, further comprising:
securing the anchoring device and lead within a patient's body.

* * * * *